United States Patent
Kelcz

(12) 
(10) Patent No.: US 6,512,943 B1
(45) Date of Patent: Jan. 28, 2003

(54) COMBINED ULTRASOUND-RADIONUCLIDE DEVICE FOR PERCUTANEOUS ULTRASOUND-GUIDED BIOPSY AND METHOD OF USE

(75) Inventor: Frederick Kelcz, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 09/576,274

(22) Filed: May 22, 2000

(51) Int. Cl.$^7$ .................................................. A61B 6/00
(52) U.S. Cl. ....................................... 600/436; 600/431
(58) Field of Search ................................. 600/436, 431

(56) References Cited

U.S. PATENT DOCUMENTS

| | | |
|---|---|---|
| 4,338,948 A | 7/1982 | Perez-Mendez et al. |
| 4,665,897 A | 5/1987 | Lemelson ................... 128/1.1 |
| 4,781,198 A | 11/1988 | Kanabrocki |
| 4,782,840 A | 11/1988 | Martin, Jr. et al. .......... 128/654 |
| 5,488,952 A | 2/1996 | Schoolman ............ 178/660.07 |
| 5,630,416 A | 5/1997 | Uchikura et al. ...... 128/660.08 |
| 5,694,933 A | 12/1997 | Madden et al. .......... 128/653.1 |
| 5,732,704 A | 3/1998 | Thurston et al. ............ 128/659 |
| 5,776,062 A | 7/1998 | Nields |
| 5,821,541 A | 10/1998 | Tümer ................... 250/370.09 |
| 5,846,200 A | 12/1998 | Schwartz ..................... 600/443 |
| 5,846,513 A | 12/1998 | Carroll et al. ............... 424/111 |
| 5,855,558 A | 1/1999 | Nakao et al. ................ 600/459 |
| 5,886,454 A | 3/1999 | Ito et al. ..................... 310/322 |
| 5,895,855 A | 4/1999 | Ishikawa et al. .............. 73/632 |
| 5,911,970 A | 6/1999 | John et al. .................. 424/1.85 |
| 5,913,857 A | 6/1999 | Ritchart et al. ................ 606/45 |
| 5,961,458 A | * 10/1999 | Carroll ........................ 600/436 |
| 6,205,352 B1 | * 3/2001 | Carroll ........................ 600/431 |

\* cited by examiner

*Primary Examiner*—Marvin M. Lateef
*Assistant Examiner*—Devaang Shah
(74) *Attorney, Agent, or Firm*—Craig A. Fieschko, Esq.; DeWitt Ross & Stevens S.C.

(57) ABSTRACT

A system and apparatus is disclosed for providing percutaneous images to assist in performing an accurate tissue biopsy and to locate nuclear medicine tracer uptake within a living being. The invention provides superimposed, simultaneous ultrasound and nuclear activity images to assist in performing accurate tissue biopsy for any procedure in which nuclear activity is used to localize possible pathological tissue. The apparatus includes a medical instrument having at least a pair of radionuclide detectors capable of detecting the depth of tracer uptake within a region of interest, which can include locating the sentinel lymph node in a breast cancer patient. The radionuclide detector is coupled to, and in operable association with, an ultrasound probe for percutaneous detection of anatomical structure about the area of maximum tracer uptake. The radionuclide detectors and the ultrasound probe are pivotally connected. The depth of the maximum tracer uptake can be determined by pivotally moving the radionuclide detectors to vary a focal point which is formed by the intersection of a line of sight from each radionuclide detector. The focal point is adjusted to the area of maximum tracer uptake by use of a visual display of radioactivity count rate or an auditory output of the radioactivity count rate. After the depth is determined and mapped, an ultrasound image is produced of the localized area. The system produces an image in which the ultrasound image is superimposed with a color representation of the tracer uptake to assist a radiologist or a surgeon in performing a tissue biopsy while avoiding vital structure.

23 Claims, 3 Drawing Sheets

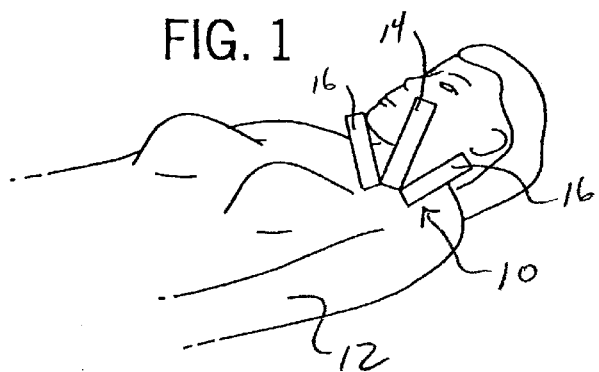
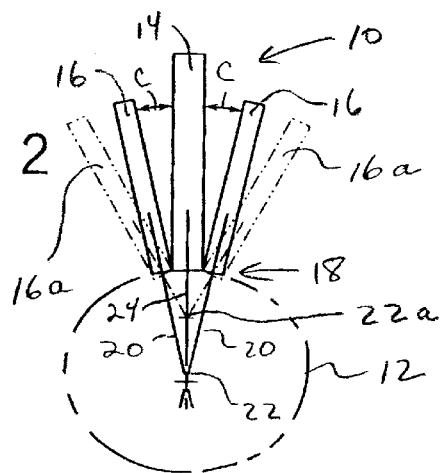
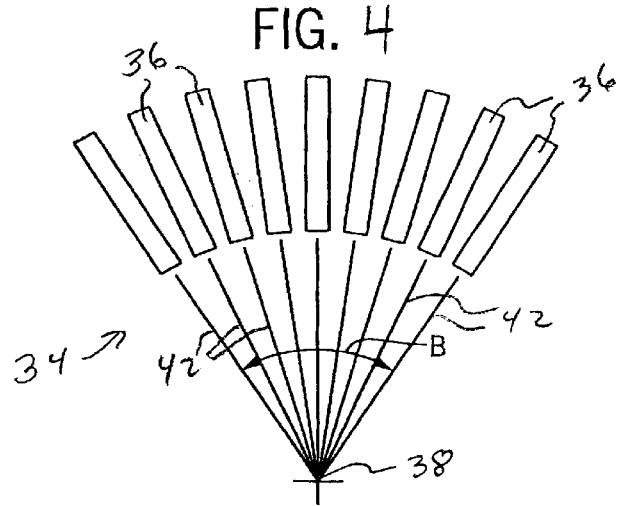

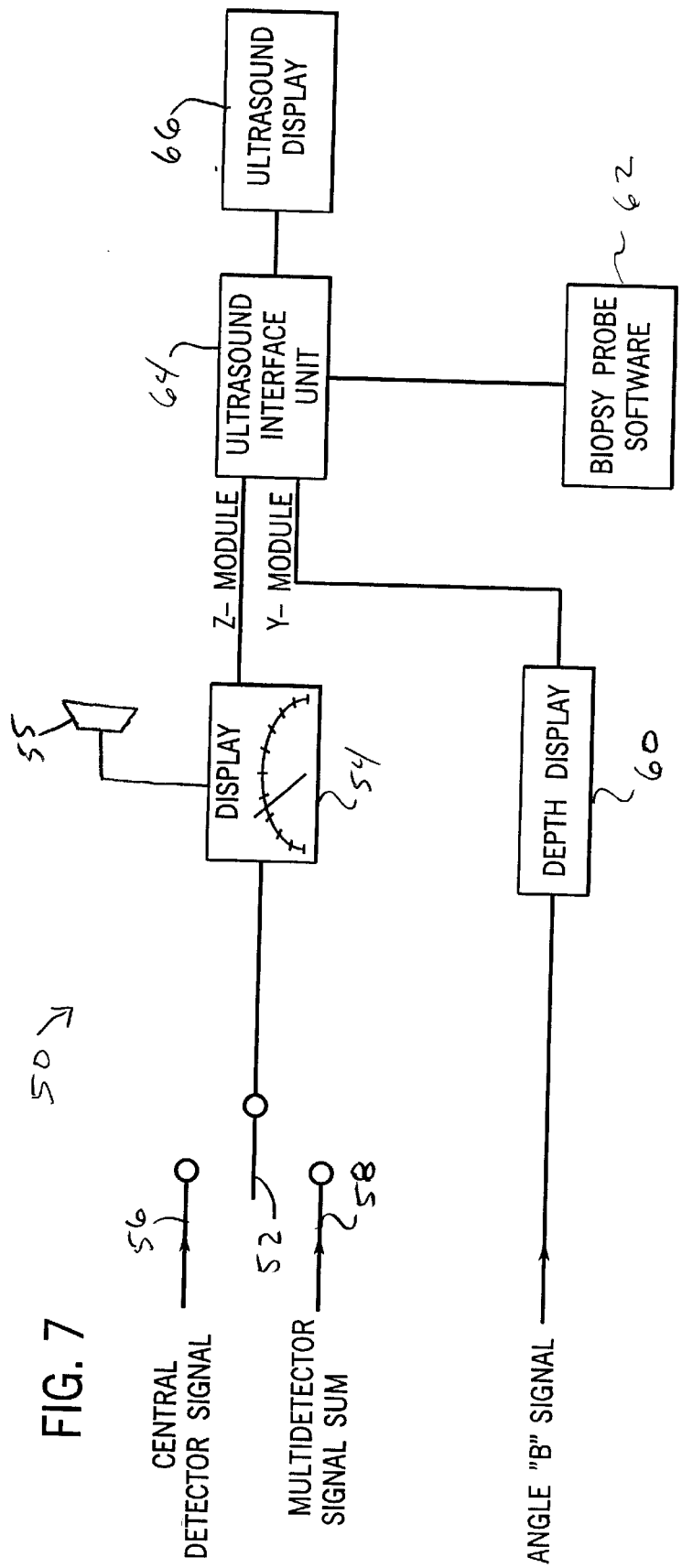

COMBINED ULTRASOUND-RADIONUCLIDE DEVICE FOR PERCUTANEOUS ULTRASOUND-GUIDED BIOPSY AND METHOD OF USE

STATEMENT REGARDING FEDERALLY SPONSORED RESEARCH OR DEVELOPMENT

This invention is made with no United States government support.

BACKGROUND OF THE INVENTION

The present invention relates generally to medical instruments and medical imaging, and more particularly to, a method and apparatus to provide percutaneous images to assist in performing an accurate tissue biopsy in which nuclear medicine tracer uptake is localized using a radionuclide detector, and then an ultrasound probe is used to obtain anatomical ultrasound images.

In breast cancer patients, the lymph node is a very common site of secondary tumor formation. Evaluation of the lymph node in the ipsilateral side of the patient is used as an early monitor of metastasis. Many patients being treated for breast cancer undergo "axillary dissection" to examine the lymph nodes. Because of their small size and diffuse distribution however, axillary dissection is surgically difficult and often physically traumatic for the patient. That is, one of the most common side effects after a patient undergoes breast cancer surgery is "lymphedema", which causes painful, and often permanent, swelling in the arm on the side of the surgery. Lymphedema results from the removal of the 10–12 lymph nodes nearest the breast. In the past, these lymph nodes were surgically removed to check for the spread of the tumor.

More recently, a technique has been employed call sentinel node biopsy. In this procedure, a small amount of radioactive dye is injected near the tumor. The blood stream leaving the tumor will carry any metastasizing cells to the first lymph node downstream. A radionuclide device, much like a Geiger counter, is then used to locate the node net the tumor, which is known as the sentinel lymph node, by monitoring trace uptake. The sentinel lymph node can then be removed and tested, If the sentinel lymph node is clear of cancerous tissue, no other nodes need to be removed. This procedure has resulted in the avoidance of the removal of all the lymph nodes in approximately two-thirds of women who have had breast cancer surgery. However, the outcome of this procedure and the effects to the patient, are largely dependent upon the palpation skills of the surgeon. The detection of the sentinel node by the Geiger counter-type device helps guide the surgeon, but is anatomically imprecise. Therefore, accurately locating the sentinel lymph nodes is critical in performing such a procedure to eliminate the chances of lymphedema and to make the procedure as non-invasive as possible. However, even with the use of the existing radionuclide probe, when a surgeon performs this procedure, it is still an open surgical procedure, and therefore more invasive than may be necessary.

It would therefore be desirable to have a method and apparatus capable of accurately tracking tracer uptake and determining the depth of maximum tracer uptake, and once the maximum tracer uptake depth is determined, imaging anatomical structure so that a tissue biopsy can be performed as non-invasively as possible.

SUMMARY OF THE INVENTION

The present invention relates to an instrument used in a method of providing percutaneous images to assist in performing an accurate tissue biopsy and a system to locate nuclear medicine tracer uptake within a living being, that overcomes the aforementioned problems.

The present invention includes a medical instrument that combines an ultrasound probe with a focusing radionuclide detector that is capable of detecting the depth of tracer uptake to perform ultrasound-guided percutaneous tissue biopsy. The area of maximum tracer uptake is localized by the medical instrument and the depth of the maximum tracer uptake is determined. The resulting image displays the radioactivity detected by the radionuclide detector as a colored representation on a typical grayscale ultrasound image. The color overlay can be either completely shut off, or faded, so that the radiologist or surgeon can perform the ultrasound-guided core biopsy using existing ultrasound biopsy software. Such software superimposes a white line, representing the expected needle track, on the ultrasound image to plan the approach to avoid vital structure and minimize the invasiveness of the procedure.

Therefore, in accordance with one aspect of the invention, a medical instrument is disclosed having an ultrasound probe capable of percutaneous detection of anatomical structure within a living being, and a radionuclide detector capable of detecting depth of tracer uptake within the living being. The radionuclide detector is coupled to, and in operable association with, the ultrasound probe such that at least one of the radionuclide detector and the ultrasound probe is pivotally moveable with respect to the other. In order to determine depth of tracer uptake, a fan array of radionuclide detectors can be used in which each of the radionuclide detectors in the fan array are pivotal with respect to one another so that a line of sight extending from each of the radionuclide detectors intersect at a moveable focal point. Alternately, a pair of radionuclide detectors can be arranged on either side of the ultrasound probe with a line of sight from each radionuclide detector converging at a moveable focal point. The moveable focal point is used to determine the precise point of maximum radioactivity.

In accordance with one aspect of the invention, a method of providing percutaneous images to assist in performing an accurate tissue biopsy includes localizing radioactivity within a portion of a living being by passing a radionuclide detector across a surface of the living being and then imaging anatomical structure within the portion of the living being with a probe on the surface of the living being about the localized radioactivity. The method also includes superimposing an image representation of the localized radioactivity with an image of the anatomical structure about the localized radioactivity.

In accordance with yet another aspect of the invention, a system is disclosed to locate nuclear medicine tracer uptake within a living being. The system includes a medical instrument having an ultrasound probe producing anatomical structure detection signals and a radionuclide detector producing nuclear detection signals. The radionuclide detector is pivotally connected to the ultrasound probe such that a line of sight from the ultrasound probe and a line of sight from the radionuclide detector converge at a focal point. The focal point is adjustable to determine a depth of tracer uptake in an anatomical structure. An interface unit is provided to integrate the anatomical structure detection signals with the nuclear medicine detection signals to provide a grayscale ultrasound image superimposed with a color image indicative of tracer uptake. A display is provided to receive the integrated anatomical structure detection signals and nuclear medicine detection signals to display the superimposed grayscale ultrasound image and color image.

By combining an ultrasound imaging and radionuclide detection imaging, in real time, a core tissue biopsy can be done under ultrasound visualization by a radiologist, rather than a surgeon, which would lower cost of the procedure while at the same time lessening the physical impact on the patient compared to axillary dissection because the exact depth of the tracer uptake can be determined. One particular application of the present invention includes locating the sentinel lymph node in a breast cancer patient in which the sentinel lymph node can be located precisely by radionuclide imaging and then ultrasound imaging can be added to perform the tissue biopsy. Such a percutaneous biopsy would be less invasive than the aforementioned radionuclide probe procedure, and although complications associated with the radionuclide probe procedure are relatively low, with this percutaneous approach, it is expected that the rate of complications would be further reduced.

Furthermore, by converting sentinel lymph node biopsy from a surgical to a radiological procedure, it is believed that the cost of the procedure can be reduced, which may permit increased access to this procedure for more women. Finally, even if the surgeon and patient decide that complete removal of the sentinel lymph node is desired instead of ultrasound-guided core biopsy, the localization method described herein can be used to guide a marking needle and hookwire into the sentinel lymph node. This is similar to the method used to localize breast lesion. The surgeon can then follow the wire directly to the lymph node, with a significant decrease in surgical dissection, resulting in decreased morbidity.

Various other features, objects and advantages of the present invention will be made apparent from the following detailed description and the drawings.

BRIEF DESCRIPTION OF THE DRAWINGS

The drawings illustrate the best mode presently contemplated for carrying out the invention.

In the drawings:

FIG. 1 is a perspective view of a human patient undergoing a procedure in accordance with and using the present invention.

FIG. 2 is a front elevational view of one embodiment of a medical instrument incorporating the present invention.

FIG. 4 is a side elevational view of the medical instrument of FIG. 3 in a first exemplary position.

FIG. 7 is a block diagram of a system for use with the present invention.

DETAILED DESCRIPTION OF THE PREFERRED EMBODIMENT

Figure 5:
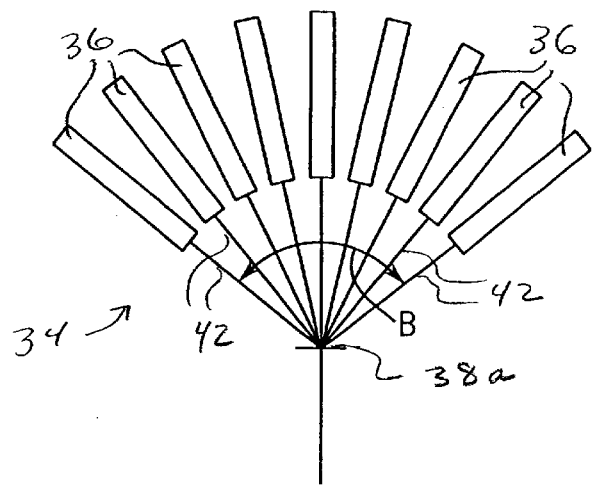
FIG. 5 is a side elevational view, similar to FIG. 4, in a secondary exemplary position.

Referring to FIG. 1, a medical imaging instrument 10 is shown in use with a living being, such as a human patient 12. In one embodiment, the medical instrument 10 of the present invention has an ultrasound probe 14 and a pair of radionuclide detectors 16. The medical instrument 10 is used in percutaneous detection of anatomical structure within the living being to detect tracer uptake within the living being. The radionuclide detectors 16 are coupled to and are in operable association with the ultrasound probe 14 such that the radionuclide detectors 16 are pivotally moveable with respect to the ultrasound probe 14. After a radioactive agent and/or a dye is injected into patient 12 near a tumor, the radionuclide detectors 16 are used to localize radioactivity within an area of interest within patient 12. Once the depth of tracer uptake is established by the radionuclide detectors 16, the ultrasound probe 14 can be used to create an image of the anatomical structure within the localized area to then obtain a tissue biopsy of the region of tracer uptake in a precise, accurate manner.

FIG. 2 shows the medical instrument 10 of FIG. 1 positioned about a phantom body 12 and depicting the pivotal moveability of the radionuclide detectors 16 with respect to the ultrasound probe 14. The medical instrument 10 has an articulation joint 18 connecting the radionuclide detectors 16 to the ultrasound probe 14 to provide pivotal movement by varying distance or angle C. The radionuclide detectors 16 are arranged about the ultrasound probe 14 such that a line of sight 20 from each radionuclide detector 16 converge at a focal point 22, together with a line of sight 24 from the ultrasound probe 14. The radionuclide detectors 16 are pivotally moveable to adjust a depth of the focal point 22. As shown, when the medical instrument 10 is in a first position, as shown in solid lines and with the radionuclide detectors 16 in close proximity to the ultrasound probe 14, the focal point 22 is at a first position, furthest from the instrument 10. When the radionuclide detectors 16a are adjusted outwardly, as shown in phantom, the focal point 22a is adjusted closer to the medical instrument 10. In this manner, the depth of the tracer uptake can be accurately indicated, as will be described in further detail with reference to FIG. 6.

Figure 3:
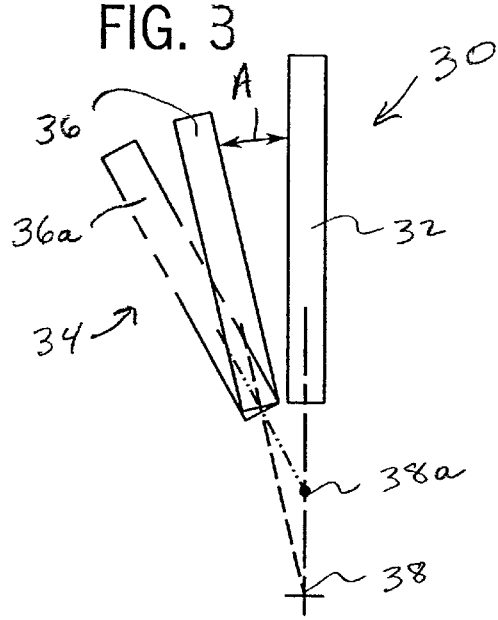
FIG. 3 is a front elevational view of another embodiment of a medical instrument incorporating the present invention.

Referring now to FIG. 3, another embodiment of a medical instrument 30 incorporating the present invention is disclosed in which a single ultrasound probe 32 is coupled to a fan array 34 of radionuclide probes 36. This arrangement allows pivotal movement between the ultrasound probe 32 and the fan array 34, as depicted by the phantom radionuclide detectors 36a. In a similar manner as that described with reference to the medical instrument of FIG. 2, the medical instrument 30 of FIG. 3 is able to focus the focal point 38 by a first adjustable angle A.

FIG. 4 shows a second adjustable angle B formed by pivotally varying the radionuclide detectors 36. In this manner, a line of sight 42 extending from each of the radionuclide detectors 36 intersect at the moveable focal point 38. As depicted in FIG. 5, when the adjustable angle B is expanded such that the radionuclide detectors 36 are pivotally moved further apart, the focal point 38a is drawn closer to the fan array 34. In this manner, this embodiment of the present invention provides two variable angles, or articulation in two planes, whereas the embodiment shown with reference to FIG. 2 provides articulation in a single plane, with a single adjustable angle. Various applications and implementations of the present invention may dictate the preference of one over the other, and it is believed that in certain applications, articulation in multiple planes may be advantageous, such as to provide more precise localization. In other applications, it is believed that a less complicated instrument, with single plane articulation, would be desired.

Figure 6:
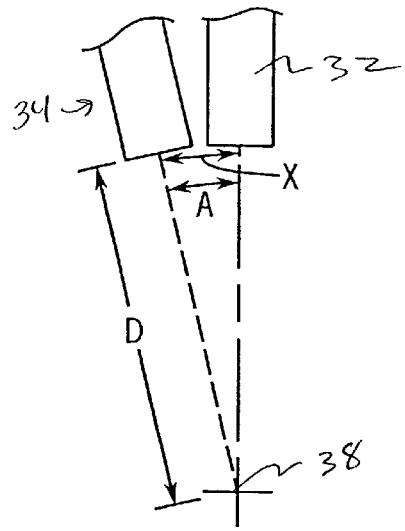
FIG. 6 is a detailed view of a portion of the medical instrument of FIG. 3.

FIG. 6 shows a detailed portion of the instrument of FIG. 3 for determining the depth D of the focal point 38. As is a well known geometric relationship, the depth D can be estimated fairly precisely by dividing the distance x between the ultrasound probe 32 and the fan array 34 by the angle A, in radians. This is true for both the angle A of FIGS. 3 and 6, or angle B of FIGS. 4 and 5, or angle C of FIG. 2.

Referring now to FIG. 7, a system 50 is disclosed to locate nuclear medicine tracer uptake within a living being. The system 50 receives signals from the previously described medical instrument 10, 30, which has an ultrasound probe producing anatomical structure detection signals and a radionuclide detector producing nuclear medicine detection signals, wherein the radionuclide detector is pivotally connected to the ultrasound probe. A line of sight from the radionuclide detector converges at a focal point with a line of sight from the ultrasound probe. The focal point is adjustable to determine a depth of tracer uptake in the anatomical structure, wherein the depth is determinable by adjusting the radionuclide detectors, as previously described. In operation, when using a fan array detector, a switch 52 is placed into a central detector mode so that a radioactivity display 54 receives signals only from the central radionuclide detector 56. It is noted that display 54 can be a visual display of radioactivity count rate or an auditory output device in which audio frequency may be transmitted directly proportional to the radioactivity count rate or a combination of both can be used to provide visual and audio cues to the radiologist that the detector 56 is nearing the lesion. An operator then scans the body to localize the radioactivity. Once the operator narrows down the search to an area having the highest radioactivity count rate, switch 52 is placed into a full detector array mode in which the display 54 is connected to receive a sum of the signals from the fan array of radionuclide detectors 58. As shown in FIGS. 4 and 5, the angle B is then varied so as to monitor count rate and move the focal point to the area of maximum activity. The angle B signal is then fed to a depth display 60 that displays the depth location of the maximum radioactivity, preferably as a digital number.

After the depth of the radioactivity is located, the fan array is canted away from the ultrasound probe until the depth of the focal point matches the depth as determined and displayed on the depth display 60. At this time, the ultrasound probe is activated 62 and provides signals to an interface unit 64 which integrates the signals from the ultrasound probe with the signals from the radionuclide detector to produce a grayscale ultrasound image superimposed with a color image indicative of tracer uptake on the ultrasound display 66.

Preferably, the interface unit 64 allows variable superimposition from having no color image of the tracer uptake with a complete grayscale ultrasound image, to having a ghost-effect color image over the grayscale ultrasound image, and to a full color image over a full grayscale ultrasound image. This allows the operator to control display of tracer uptake over the ultrasound grayscale image. Alternatively, the color display could automatically be switched on/off periodically to a momentarily display only the grayscale ultrasound image, or a switch can be provided to manually switch the color display representation on/off. This will allow an operator, such as a radiologist, to better see the anatomical structure associated with the radioactivity during the biopsy.

It is understood that the size of the colored tracer uptake area will be established by design choice and will be related to individual probe aperture and the number of probes chosen. The more probes in the fan array and the smaller the diameter of each probe aperture, the more precise the medical instrument would be in locating the source of radioactivity. Once the precise location of the maximum radioactivity has been determined, the radionuclide detectors can be deactivated and preexisting ultrasound biopsy software can be used to superimpose a directional line, representing the expected needle track, on the ultrasound image for the biopsy procedure. The radiologist or surgeon can then plan the approach of the biopsy so as to avoid vital structure and greatly reduce any ill side effects from a biopsy.

Accordingly, the present invention includes a method of providing percutaneous images to assist in performing an accurate tissue biopsy that includes localizing radioactivity within a portion of a living being by passing a radionuclide detector across a surface of the living being and then imaging anatomical structure within the portion of the living being with a probe on the surface of the living being about the localized radioactivity. The method also includes superimposing an image of the anatomical structure about the localized radioactivity with an image representation of the localized radioactivity. The step of localizing radioactivity is further defined to include first scanning a general area to localize radioactivity, and then determining a depth of the radioactivity from the surface using at least two radionuclide detectors arranged so that a line of sight from each radionuclide detector converges at a focal point. The depth is then determined by using well known triangulation techniques. The method further includes displaying the depth of the radioactivity from the surface, preferably as a digital number, to assist a radiologist or surgeon in performing a tissue biopsy.

In localizing the radioactivity, the method can include using a central radionuclide detector centralized within an array of radionuclide detectors to scan the general area, and then using a sum output of each of the radionuclide detectors in the array of radionuclide detectors to determine the depth of the radioactivity. The step of using each of the radionuclide detectors in the array of detectors further includes varying an angle formed by the array of radionuclide detectors in order to adjust the focal point to the correct depth of the maximum radioactivity.

The step of imaging anatomical structure is further defined as imaging anatomical structure using an ultrasound probe pivotally mounted to the radionuclide detector, and the step of superimposing an image, includes superimposing a grayscale ultrasound image with a colored nuclear activity image. The method also includes the step of providing a variable user control of the colored nuclear activity image to allow a user to focus on the grayscale ultrasound image with or without the colored nuclear activity image.

The present invention has been described in terms of the preferred embodiment, and it is recognized that equivalents, alternatives, and modifications, aside from those expressly stated, are possible and within the scope of the appending claims.

What is claimed is:

1. A medical instrument comprising:
   an ultrasound probe capable of percutaneous detection of anatomical structure within a living being;
   a radionuclide detector capable of detecting depth of tracer uptake within the living being; and
   wherein the radionuclide detector is coupled to, and in operable association with, the ultrasound probe such that at least one of the radionuclide detector and the ultrasound probe is pivotally moveable with respect to the other.

2. The instrument of claim 1 further comprising an articulation joint connecting the radionuclide detector to the ultrasound probe to provide the pivotal movement.

3. The instrument of claim 1 further comprising a plurality of radionuclide detectors arranged in a fan array and connected to the ultrasound probe.

4. The instrument of claim 3 wherein the plurality of radionuclide detectors are pivotal with respect to one another to form a first adjustable angle so that a line of sight extending from each of the plurality of radionuclide detectors intersect at a moveable focal point, wherein the focal point is adjustable to localize nuclear activity of the tracer uptake.

5. The instrument of claim 4 wherein the fan array of radionuclide detectors is pivotal with regard to the ultrasound probe to form a second adjustable angle so that the lines of sight extending from the fan array of radionuclide detectors intersect with a line of sight from the ultrasound probe at the moveable focal point.

6. The instrument of claim 1 further comprising a second radionuclide detector, wherein each radionuclide detector is arranged about the ultrasound probe such that a line of sight from each radionuclide detector converges at a focal point.

7. The instrument of claim 6 wherein the ultrasound probe has a line of sight that converges with the focal point of the radionuclide detectors and wherein the radionuclide detectors are pivotally moveable to adjust a depth of the focal point.

8. The instrument of claim 1 further comprising a radioactivity output device to receive radioactivity intensity signals and provide a radioactivity count rate indication.

9. The instrument of claim 1 further comprising a display unit to display an ultrasound image of anatomical structure superimposed with a color image of radioactivity of tracer uptake.

10. A method of providing percutaneous images to assist in performing an accurate tissue biopsy comprising:

localizing radioactivity within a portion of a living being by passing a radionuclide detector across a surface of the living being;

imaging anatomical structure within the portion of a living being with a probe on the surface of the living being about the localized radioactivity; and superimposing an image representation of the localized radioactivity with an image of the anatomical structure about the localized radioactivity.

11. The method of claim 10 wherein the step of localizing radioactivity comprises first scanning a general area to generally localize radioactivity, and then determining a depth of the radioactivity from the surface of the living being using at least two radionuclide detectors.

12. The method of claim 11 further comprising the step of displaying the depth of the radioactivity from the surface.

13. The method of claim 11 wherein the step of localizing radioactivity further comprises the step of using a central radionuclide detector centralized within an array of radionuclide detectors to scan the general area and then using each of the radionuclide detectors in the array of radionuclide detectors to determine the depth of the radioactivity.

14. The method of claim 13 wherein the step of using each of the radionuclide detectors in the array of radionuclide detectors further comprises varying an angle formed within the array of radionuclide detectors.

15. The method of claim 10 wherein the step of imaging is further defined as imaging anatomical structure using an ultrasound probe pivotally mounted with the radionuclide detector.

16. The method of claim 15 wherein the step of superimposing an image includes superimposing a grayscale ultrasound image with a colored nuclear activity image, and further comprises the step of providing a variable user control of the colored nuclear activity image to allow a user to focus on the grayscale ultrasound image with and without the colored nuclear activity image.

17. A system to locate nuclear medicine tracer uptake within a living being comprising:

a medical instrument having an ultrasound probe producing anatomical structure detection signals and a radionuclide detector producing nuclear medicine detection signals, wherein the radionuclide detector is pivotally connected to the ultrasound probe such that a line of sight from the ultrasound probe and a line of sight from the radionuclide detector converge at a focal point, wherein the focal point is adjustable to determine a depth of tracer uptake in anatomical structure;

an interface unit to integrate the anatomical structure detection signals with the nuclear medicine detection signals to provide a grayscale ultrasound image superimposed with a color image indicative of tracer uptake; and a display receiving the integrated anatomical structure detection signals and nuclear medicine detection signals and display the superimposed grayscale ultrasound and color imagery.

18. The system of claim 17 wherein the interface unit allows variable superimposition from having no color image and complete grayscale ultrasound image, to ghost-effect color image over complete grayscale ultrasound image, and to full color image over complete grayscale ultrasound image.

19. The system of claim 17 further comprising a plurality of radionuclide arranged in a fan array and connected to the ultrasound probe.

20. The system of claim 19 wherein the plurality of radionuclide detectors are pivotal with regard to one another to form a first adjustable angle so that a line of sight extending from each of the plurality of radionuclide detectors intersect at a moveable focal point, wherein the focal point is adjustable to localize nuclear activity of the tracer uptake.

21. The system of claim 20 wherein the fan array of radionuclide detectors is pivotal with regard to the ultrasound probe to form a second adjustable angle so that the lines of sight extending from the fan array of radionuclide detectors intersect with a line of sight from the ultrasound probe at the moveable focal point.

22. The system of claim 17 comprising a second radionuclide detector, wherein each radionuclide detector is arranged about the ultrasound probe such that a line of sight from each radionuclide detector converges at a focal point.

23. The system of claim 22 wherein the ultrasound probe has a line of sight that converges with the focal point of the radionuclide detectors and wherein the radionuclide detectors are pivotally moveable to adjust a depth of the focal point.

* * * * *